United States Patent [19]

Dichtelmüller et al.

[11] Patent Number: 4,946,648

[45] Date of Patent: Aug. 7, 1990

[54] METHOD OF STERILIZING PLASMA OR PLASMA FRACTIONS

[75] Inventors: Herbert Dichtelmüller, Sulzbach; Wolfgang Möller, Oberursel; Wolfgang Stephan, Dreieich; Hans Schleussner, Frankfurt am Main, all of Fed. Rep. of Germany

[73] Assignee: Biotest Pharma GmbH, Dreieich, Fed. Rep. of Germany

[21] Appl. No.: 241,300

[22] Filed: Sep. 7, 1988

[30] Foreign Application Priority Data

Sep. 11, 1987 [DE] Fed. Rep. of Germany ....... 3730533

[51] Int. Cl.$^5$ .................. A61L 2/10; A61L 2/18; C07K 15/06
[52] U.S. Cl. .................. 422/24; 250/455.1; 422/28; 424/530; 435/2; 530/380; 530/383; 530/830; 530/831
[58] Field of Search ............. 422/24, 28; 435/2; 530/380, 383, 830, 831; 424/101; 250/455.1

[56] References Cited

U.S. PATENT DOCUMENTS

| 4,314,997 | 2/1982 | Shanbrom | 424/101 |
| 4,315,919 | 2/1982 | Shanbrom et al. | 424/101 X |
| 4,370,264 | 1/1983 | Kotitschke et al. | 530/383 |
| 4,540,573 | 9/1985 | Neurath et al. | 530/380 X |
| 4,789,545 | 12/1988 | Woods et al. | 424/89 X |

FOREIGN PATENT DOCUMENTS 3033932  5/1984  Fed. Rep. of Germany ...... 530/383

OTHER PUBLICATIONS

Block, Seymour S., *Disinfection, Sterilization and Preservation*, Lea & Febiger, 1983, p. 107.

Horowitz et al, "Inactivation of Viruses in Labile Blood Derivatives", Transfusion 25 (1985), pp.516–522.

*Primary Examiner*—Robert J. Warden
*Assistant Examiner*—Jill Johnston
*Attorney, Agent, or Firm*—Sprung, Horn, Kramer & Woods

[57] ABSTRACT

A method of sterilizing plasma or plasma fractions, including fractions that contain the blood-coagulating Factor VIII by treatment with β-propiolactone or ultraviolet radiation. Treatment with tri-n-butyl phosphate and sodium cholate or Tween 80 is carried out either prior to or simultaneously with the β-propiolactone treatment or ultraviolet radiation.

13 Claims, No Drawings

METHOD OF STERILIZING PLASMA OR PLASMA FRACTIONS

The invention relates to a method of sterilizing plasma or plasma fractions, including preparations that contain the blood-coagulating Factor VIII.

Human plasma or derivatives prepared therefrom contain potential human-pathenogenic viruses that expose the recipient of the preparations to the risk of infection with hepatitis virus B (HVB), hepatitis non-A/non-B virus (HNANBV), or human immunodeficiency virus (HIV, the AIDS virus). Human plasma preparations must accordingly be effectively sterilized, by heat, chemicals, or radiation for example. Heat treatment is not appropriate for preparations that contain coagulation factors, which are destroyed even when subjected to a temperature of 60 ° C. for one hour.

G. A. LoGrippo et al. (*Chemical and combined methods for plasma sterilization*, Bibl. Haematol., Vol. 7 [1958], 225–30) propose a method of sterilization combining treatment with β-propiolactone with ultraviolet radiation. This method very effectively inactivates not only the relevant human pathenogenic viruses HBV, HNANBV, and HIV but also bacteriophages, Sendai virus, and many other viruses independent of their size, genome, or surface structure. Furthermore, both RNA and DNA viruses and viruses with lipid envelopes ("lipid" viruses) or protein envelopes ("protein" viruses) are inactivated. The effectiveness of the β-propiolactone plus ultraviolet radiation method is so high, however, that the activity of sensitive plasma proteins, especially the blood-coagulation Factor VIII, is also reduced. It has accordingly been impossible up to now to sterilize Factor VIII and obtain a satisfactory yield, although such other plasma proteins as serum preserve, prothombin complex (PPSB), or fibrinogen have been successfully subjected to this method.

β-Propiolactone reacts with RNA (ribonucleic acid) or DNA (desoxyribonucleic acid) and to a lesser extent with proteins, and decomposes in a third reaction with water into β-hydroxypropionic acid.

Ultraviolet radiation destroys RNA and DNA by both intramolecular reactions and fission. The more dilute the protein solution and the lower the optical density at 254 nm, the more effective the ultraviolet radiation.

German Patent No. 3 033 932 discloses a method of cold-sterilizing preparations that contain blood-coagulating Factor VIII. The protein solution that contains the Factor VIII is subjected to a four-step process. It is treated with a non-ionogenic tenside, irradiated with ultraviolet light, treated with β-propiolactone, and adsorbed over colloidal silicic acid. Even this complicated procedure, however, does not yield enough active Factor VIII.

Another method of cold sterilization is known from Transfusion 25 (1985), 6, 516–22. Viruses with lipid envelopes (lipid viruses) are inactivated by treating them with tri-n-butyl phosphate plus sodium cholate (TNBP/SC). Although inactivation of HBV, HNANBV, and HIV has been demonstrated for this method and although Factor VIII can be sterilized without decisive loss of activity by its means, the method will not inactivate viruses with envelopes that do not contain lipid constituents. "Protein" viruses (e.g. Φx174) are not inactivated, and the method is limited to lipid viruses.

The object of the present invention is accordingly to provide a method of sterilizing plasma or plasma fractions that contain the blood-coagulating Factor VIII by treatment with β-propiolactone or ultraviolet radiation that will on the one hand improve the yield of Factor VIII activity and on the other inactivate both human-pathenogenic lipid viruses and human-pathenogenic protein viruses.

This object is attained by treating with tri-n-butyl phosphate and sodium cholate or Tween 80 either prior to or simultaneously with the β-propiolactone treatment or ultraviolet radiation.

It has, surprisingly, been discovered that the combination of treatment with β-propiolactone or ultraviolet radiation plus treatment with tri-n-butyl phosphate and sodium cholate or Tween 80 (polyoxyethylene-20 sorbitan monooleate) in accordance with the invention results in a drastic and synergistic increase in the inactivation of lipid and protein viruses even though tri-n-butyl phosphate and sodium cholate or Tween 80 alone are almost or completely ineffective against protein viruses. The tri-n-butyl phosphate and sodium cholate or Tween 80 apparently eliminate the β-propiolactone-destroying activity in the plasma or plasma fractions and accordingly significantly increases the effectiveness of the β-propiolactone. The synergism of the ultraviolet radiation with the tri-n-butyl phosphate and sodium cholate or Tween 80 might also derive from a certain destabilization of the protein and lipid viruses by the solvent and detergent. The inclusion of ultraviolet radiation leads to greater inactivation than would the sum of the individual steps alone. Furthermore, the combination sterilization method in accordance with the invention does not essentially decrease Factor VIII activity.

The sterilization method in accordance with the invention can be carried out with plasma, i.e. human blood plasma and plasma fractions. Cryoprecipitate or a Cohn Fraction I can be employed as the fractions that contain the blood-coagulating Factor VIII. The sterilization is carried out at a pH of 4.5 to 8.3, preferably at a pH of 7.2, and at a temperature of +4° to 37° C., preferably at 23° C. The treatment with tri-n-butyl phosphate and sodium cholate or Tween 80 is carried out either prior to or simultaneously with the β-propiolactone treatment or ultraviolet radiation. It is preferable initially to incubate with tri-n-butyl phosphate and sodium cholate or Tween 80 for 60 to 90 minutes and then treat with β-propiolactone for another 60 to 90 minutes or irradiate with ultraviolet light. The tri-n-butyl phosphate is employed at a concentration of 0.05 to 0.5 %, preferably 0.3 %, and the sodium cholate at a concentration of 0.03 to 0.4 %, preferably 0.2 %. The percentages refer to weight per volume, e.g. 0.05 to 0.5 % means 0.06 to 0.5 gram per 100 ml of plasma. When Tween 80 is employed instead of the cholate, it is employed at a concentration of preferably 1 %. The β-propiolactone is employed in a concentration of 0.01 to 0.3 %. When a fraction that contains Factor VIII is to be sterilized, the β-propiolactone is employed at a concentration of 0.01 to 0.25 %, preferably 0.05 %. The pH is maintained constant by adding sodium hydroxide solution.

The irradiation with ultraviolet light is carried out at a high enough intensity to ensure sufficient inactivation of the viruses. The irradiation can for example be carried out in a continuous-flow rotating device with two 20 W ultraviolet lamps at a flow rate of 20 liters per hour, with a layer 1 mm thick, and at a distance of 1 cm.

The following examples will demonstrate that the activity of the Factor VIII is not essentially reduced by the combination method in accordance with the invention and that the inactivation of protein viruses is much higher as the result of treatment with β-propiolactone or ultraviolet radiation following or simultaneously with treatment with tri-n-butyl phosphate and sodium cholate or Tween 80 in comparison with inactivation with β-propiolactone or ultraviolet radiation alone even though treatment with tri-n-butyl phosphate and sodium cholate or Tween 80 alone is almost or completely ineffective with regard to such inactivation.

The function of the tri-n-butyl phosphate and sodium cholate or tri-n-butyl phosphate and Tween 80 is accordingly not in this case to inactivate the viruses but to increase the effectiveness of the β-propiolactone or ultraviolet radiation.

The invention will now be specified with reference to the following examples.

EXAMPLE 1

100 ml of human plasma, freed of cryoprecipitate, were treated with 0.3 % tri-n-butyl phosphate and 0.2 % sodium cholate and left for 60 minutes at pH 7.2 and 23° C.

50 μl of β-propiolactone (0.05 %) were added and the plasma incubated another 60 minutes at pH 7.2 and 23° C. The Factor VIII activity was measured after the β-propiolactone had an opportunity to act with and without tri-n-butyl phosphate. 78 % of the Factor VIII activity remained in the plasma subsequent to treatment with β-propiolactone, 58 % subsequent to treatment with tri-n-butyl phosphate and sodium cholate, and 62 % subsequent to treatment with the combination (100 % in the untreated control batch).

EXAMPLE 2

100 ml of plasma were preliminarily treated as described in Example 1 with tri-n-butyl phosphate and sodium cholate and then sterilized with β-propiolactone. The inactivation of the previously added bacteriophage Φx 174 was compared with that in the plasma not previously treated with tri-n-butyl phosphate and sodium cholate. An increase in Φx 174 inactivation of approximately 72 000 times was realized in comparison with the plasma not previously treated with tri-n-butyl phosphate and sodium cholate and sterilized with β-propiolactone.

EXAMPLE 3

100 ml of cryoprecipitate (Factor VIII) dissolved in 0.15 M glycine were treated with 50 μof β-propiolactone (0.05 %) and incubated 90 minutes at pH 7.2 and 23° C.

The inactivation of the previously added bacteriophage Φx 174 was measured. There was an almost 20-fold increase in inactivation as the result of the combination treatment with tri-n-butyl phosphate and sodium cholate plus treatment with β-propiolactone in contrast to treatment with β-propiolactone alone.

EXAMPLE 4

100 ml of Factor VIII concentrate dissolved in 0.15 sodium chloride was treated with 0.3 % tri-n-butyl phosphate and 0.2 % sodium cholate and incubated 60 minutes at pH 7.2 and 23° C. 50 μl of β-propiolactone (0.05 %) were added and the solution incubated 90 minutes at pH 7.2 and 23° C. Table 1 indicates the yield of Factor VIII activity subsequent to β-propiolactone treatment following incubation with tri-n-butyl phosphate and sodium cholate. Almost all of the Factor VIII activity remains.

EXAMPLE 5

100 ml of plasma or Factor VIII concentrate at a time were treated with bacteriophage Φx 174 and sterilized with β-propiolactone (0.05 %) both with and without preliminary treatment with tri-n-butyl phosphate and sodium cholate. The results are also illustrated in Table 1.

Since bacteriophage Φx 174 lacks a lipid envelope it is as expected not inactivated by the tri-n-butyl phosphate and sodium cholate. What is observed, however, is a definite increase in the virucidal activity of the βpropiolactone as the result of the preliminary treatment with tri-n-butyl phosphate and sodium cholate.

TABLE 1

Inactivation of φx 174 by means of 0.2% of tri-n-butyl phosphate (TNBP) and 0.3% sodium cholate (SC), of β-propiolactone (β-PL), and of a combination of β-propiolactone with tri-n-butyl phosphate and sodium cholate

| Preparation | Treatment | Inactivation of φx 174 (log$_{10}$) | Increased effectiveness | Yield of Factor VIII (%) |
|---|---|---|---|---|
| Plasma | 0.25% β-PL | 1.16 | — | 78 |
| | TNBP & SC | 0.20 | — | 58 |
| | TNBP & SC + 0.05% β-PL | 3.71 | x 355 | 62 |
| | untreated control | — | — | 100 |
| Plasma | 0.25% β-PL | 2.30 | — | — |
| | TNBP & SC | 0.02 | — | — |
| | TNBP & SC + 0.25% β-PL | 7.16 | x 72440 | — |
| | untreated control | — | — | — |
| Factor VIII | 0.05% β-PL | 0.78 | — | 95 |
| | TNBP & SC | 0.16 | — | 100 |
| | TNBP & SC + 0.05% β-PL | 2.04 | x 18 | 93 |
| | untreated control | — | — | 100 |

EXAMPLE 6

100 ml Factor VIII concentrate at a time were treated with bacteriophage Kappa and irradiated with ultraviolet light (two 20 W tubes) both with and without preliminary treatment with 0.3 % tri-n-butyl phosphate and 1 % Tween 80. The samples that had not been preliminarily treated were treated with tri-n-butyl phosphate and Tween 80 subsequent to irradiation. Table 2 lists the results.

TABLE 2

| Treatment | Inactivation of Kappa (log$_{10}$) | Yield of Factor VIII (%) |
|---|---|---|
| UV | 3.6 | — |
| UV + TNBP & Tween 80 | 3.8 | 79 |
| TNBP & Tween 80 | 0.4 | — |
| TNBP & Tween 80 + UV | 5.4 | 74 |

Treatment with tri-n-butyl phosphate and Tween 80 followed by ultraviolet irradiation (log 5.4) is accordingly approximately 60 times as effective in inactivating the protein virus Kappa as ultraviolet irradiation alone (log 3.6). tri-n-Butyl phosphate and Tween 80 alone is almost without effect.

It is understood that the specification and examples are illustrative but not limitative of the present invention and that other embodiments within the spirit and scope of the invention will suggest themselves to those skilled in the art.

What is claim is:

1. In a method of sterilization of plasma or plasma fractions, including fractions that contain the blood-coagulating Factor VIII, by treatment with β-propiolactone, the improvement which comprises additionally treating the plasma or fractions with tri-n-butyl phosphate and sodium cholate either prior or simultaneously with the β-propiolactone treatment.

2. A method according to claim 1, wherein the sterilization is carried out at a pH of about 4.5 to 8.3 and at a temperature of about +4° to 37° C.

3. A method according to claim 1, wherein the additional treatment is effected with tri-n-butyl phosphate at a concentration of about 0.05 to 0.5 % and sodium cholate at a concentration of about 0.03 to 0.4 %.

4. A method according to claim 1, wherein the additional treatment is effected with tri-n-butyl phosphate at a concentration of about 0.3 % and sodium cholate at a concentration of about 0.2 %.

5. A method according to claim 1, wherein sterilization is effected with β-propiolactone at a concentration of about 0.01 to 0.3 %.

6. A method according to claim 1, wherein the sterilization is carried out at a pH of about 7.2 and a temperature of about 23° C.

7. A method according to claim 1, wherein the plasma or plasma fractions that are being sterilized contain the blood-coagulating Factor VIII and the sterilization is effected with β-propiolactone at a concentration of about 0.01 to 0.25 %.

8. A method according to claim 1, wherein sterilization is effected with β-propiolactone at a concentration of about 0.05 %.

9. In a method of sterilization of plasma or plasma fractions, including fractions that contain the blood-coagulating Factor VIII, by treatment with ultraviolet radiation, the improvement which comprises additionally treating the plasma or fractions with tri-n-butyl phosphate and polyoxyethylene-20 sorbitan monooleate either prior to or simultaneously with the ultraviolet radiation.

10. A method according to claim 9, wherein the additional treatment is effected with tri-n-butyl phosphate at a concentration of about 0.3 % and the polyoxyethylene-20 sorbitan monooleate at a concentration of about 0.15 to 2 %.

11. A method according to claim 9, wherein the sterilization is effected with ultraviolet irradiation at 254 nm.

12. A method according to claim 9, wherein the sterilization is carried out at a pH of about 4.5 to 8.3 and at a temperature of about +4° to 37° C.

13. A method according to claim 9, wherein the sterilization is carried out at a pH of about 7.2 and a temperature of about 23° C.

* * * * *